United States Patent [19]

Caracciolo

[11] Patent Number: 4,827,727
[45] Date of Patent: May 9, 1989

[54] CARCASS CHILLER AND STERILIZER

[76] Inventor: Louis D. Caracciolo, 267A Hayesmill Rd., Atco, N.J. 08004

[21] Appl. No.: 153,807

[22] Filed: Feb. 8, 1988

[51] Int. Cl.$^4$ ............................................. F25D 13/06
[52] U.S. Cl. ......................................... 62/63; 62/78; 62/264; 62/375
[58] Field of Search ..................... 62/63, 78, 264, 374, 62/375

[56] References Cited

U.S. PATENT DOCUMENTS

| | | | |
|---|---|---|---|
| 1,538,369 | 5/1925 | Akiyama . | |
| 3,025,170 | 3/1962 | Murphy et al. | 99/194 |
| 3,421,836 | 1/1969 | Dundin et al. | 99/194 |
| 3,745,026 | 7/1973 | Hansen et al. | 99/194 |
| 4,245,483 | 1/1981 | Murai | 62/376 |
| 4,517,159 | 5/1985 | Karlson | 422/20 |
| 4,627,924 | 12/1986 | Coste | 210/760 |
| 4,666,722 | 5/1987 | Creed et al. | 426/393 |

OTHER PUBLICATIONS

Barker International Mark IV, V and VI Chiller, Two Systems in One.
Sheldon, B. W. and Brown A. L., "Efficacy of Ozone as a Disinfectant for Poultry Carcasses and Chill Water", vol. 51, No. 2, 1986, Journal of Food, Science 305.
Kaess G. and Weidemann, J. F., "Ozone Treatment of Chilled Beef", 1968, Journal of Food Technology, pp. 325–334.

Primary Examiner—Ronald C. Capossela
Attorney, Agent, or Firm—Kenyon & Kenyon

[57] ABSTRACT

An apparatus and method for sterilizing and chilling animal carcasses is provided comprising a tank for holding water, a means for cooling water in the tank, piping for carrying contaminated water out of the tank, a means for injecting ozone into the water of the apparatus, a means for purifying contaminated water in the piping, piping for returning purified water back to the tank and a means for decomposing gaseous ozone which escapes from the water in the tank before the gas is liberated into the atmosphere. The ozone destroys all forms of harmful microorganisms in the carcasses and the water. Because the water of the system is sterilized it can be disposed of easily.

25 Claims, 2 Drawing Sheets

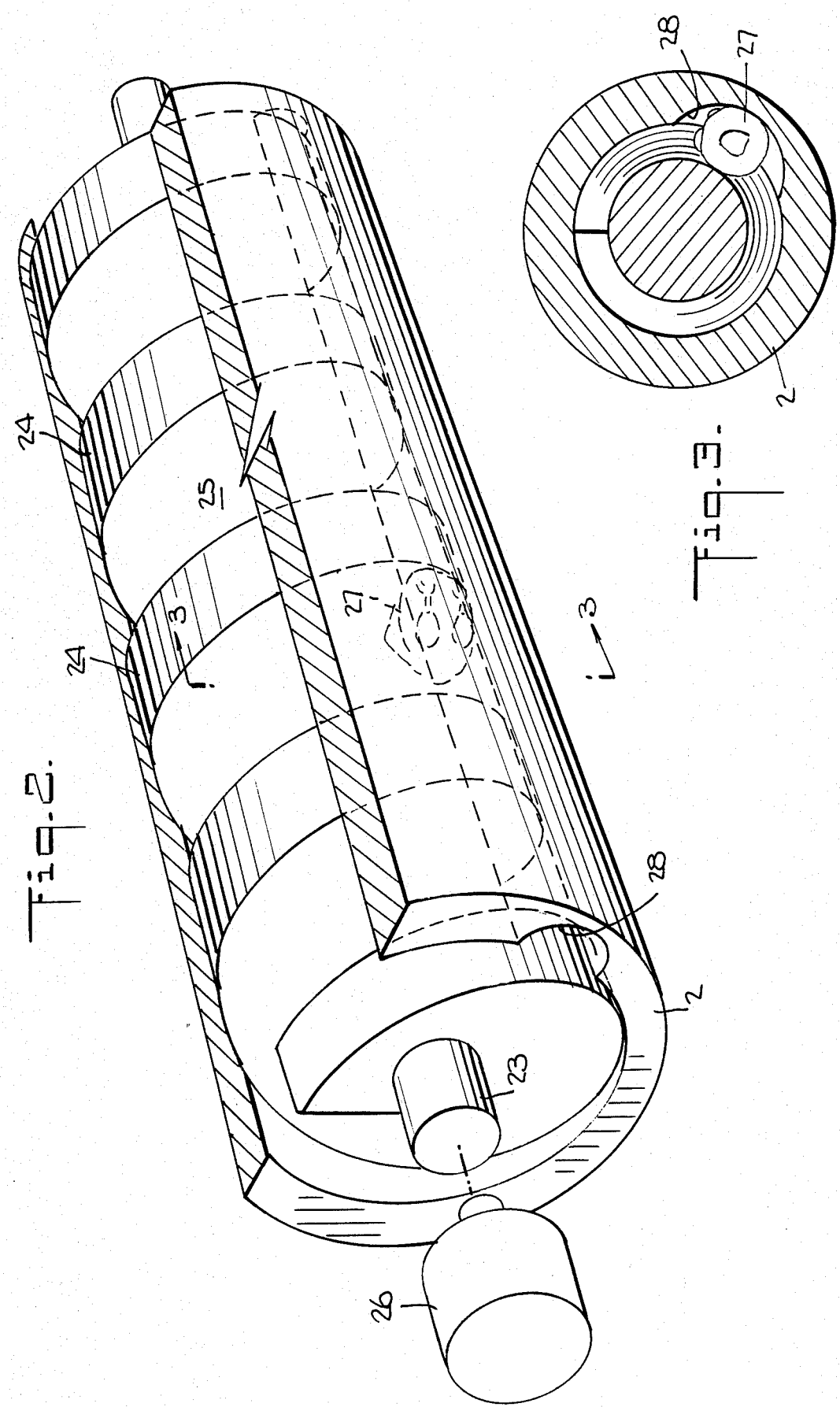

CARCASS CHILLER AND STERILIZER

The invention relates to an apparatus and method for chilling and sterilizing animal carcasses in the meat industry. More particularly, the invention relates to an apparatus for chilling and sterilizing poultry with ozonated water in which the ozonated water is continuously cleaned and recirculated through the apparatus.

It is customary in the poultry processing industry to ship live birds to a plant where they are bled, scalded, defeathered and eviscerated. Scalding operations are usually carried out at 128 degrees Fahrenheit so that the eviscerated birds must be subsequently chilled prior to packaging and shipping. It is the custom of the industry to chill the birds in an open tank containing a mixture of ice and water for a period of about 4 to 24 hours. The water chilling step is also conducted for the purpose of cleaning away most of the internal and external bacteria of the birds prior to packaging. After the birds have been chilled to a body temperature of about 33 to 40 degrees Fahrenheit they are usually packed in crates with ice and shipped.

The forementioned procedure suffers from two major drawbacks. First, the water bath is quickly contaminated with fecal matter, escherichia coli and salmonellae from the birds. These contaminants are eventually distributed throughout the wash bath and contaminate all of the carcasses moving through the system. Second, the contaminated water presents a serious disposal problem. Processors incur substantial toll charges when dumping the contaminated water into either private lagoons or municipal sewer systems.

The industry and the USDA have dealt with these problems by requiring that an additional half gallon of water (or four pounds of ice) be added to the chiller for each bird which enters the system. Although this procedure can maintain the contaminant concentration of the water at a certain level, the process is extremely inefficient because enormous quantities of water are necessary. Moreover, the procedure does not obviate the water disposal problem.

The industry has further dealt with the problem by constructing chillers with an overflow feature which acts as a skimmer to remove water containing fat particles from the chiller. However, chillers constructed with such overflow features also require enormous amounts of water and a floor drain. Because dirty water flows onto the floor these types of chillers result in unsanitary working conditions.

Accordingly, it is an object of the invention to provide an apparatus for sterilizing and chilling animal carcasses in which additional water need not be added to the system when a new carcass is added.

It is another object of the invention to provide an apparatus for sterilizing and chilling animal carcasses in ozonated water.

It is a further object of the invention to provide an apparatus for sterilizing and chilling animal carcasses in which the chill water is purified and recirculated through the apparatus.

SUMMARY OF THE INVENTION

An apparatus and method for sterilizing and chilling animal carcasses is provided comprising a tank for holding water, a means for cooling water in the tank, outlet piping for carrying contaminated water away from the tank, an ozone generator, an ozone injection system for injecting ozone into the water in the apparatus, a means for purifying the water from the outlet piping, inlet piping for returning purified water back to the tank, and a means for decomposing gaseous ozone, which escapes from the water in the tank, before the gas is released into the atmosphere. The apparatus is a continuous system which efficiently sterilizes and chills carcasses placed in the tank without the need for adding more water as additional carcasses are placed in the tank. The ozone destroys all forms of harmful microorganisms in the carcasses and the water. Because the water of the system is sterilized it can be disposed of easily.

Other Objects and advantages will become apparent upon reading the following detailed description with the accompanying drawings, wherein:

FIG. 2 is a cross sectional view of the inside of a tank of the invention equipped with a screw means for moving carcasses through the tank, and FIG. 3 is another view of the tank depicted in FIG. 2.

DETAILED DESCRIPTION OF THE INVENTION

Figure 1:
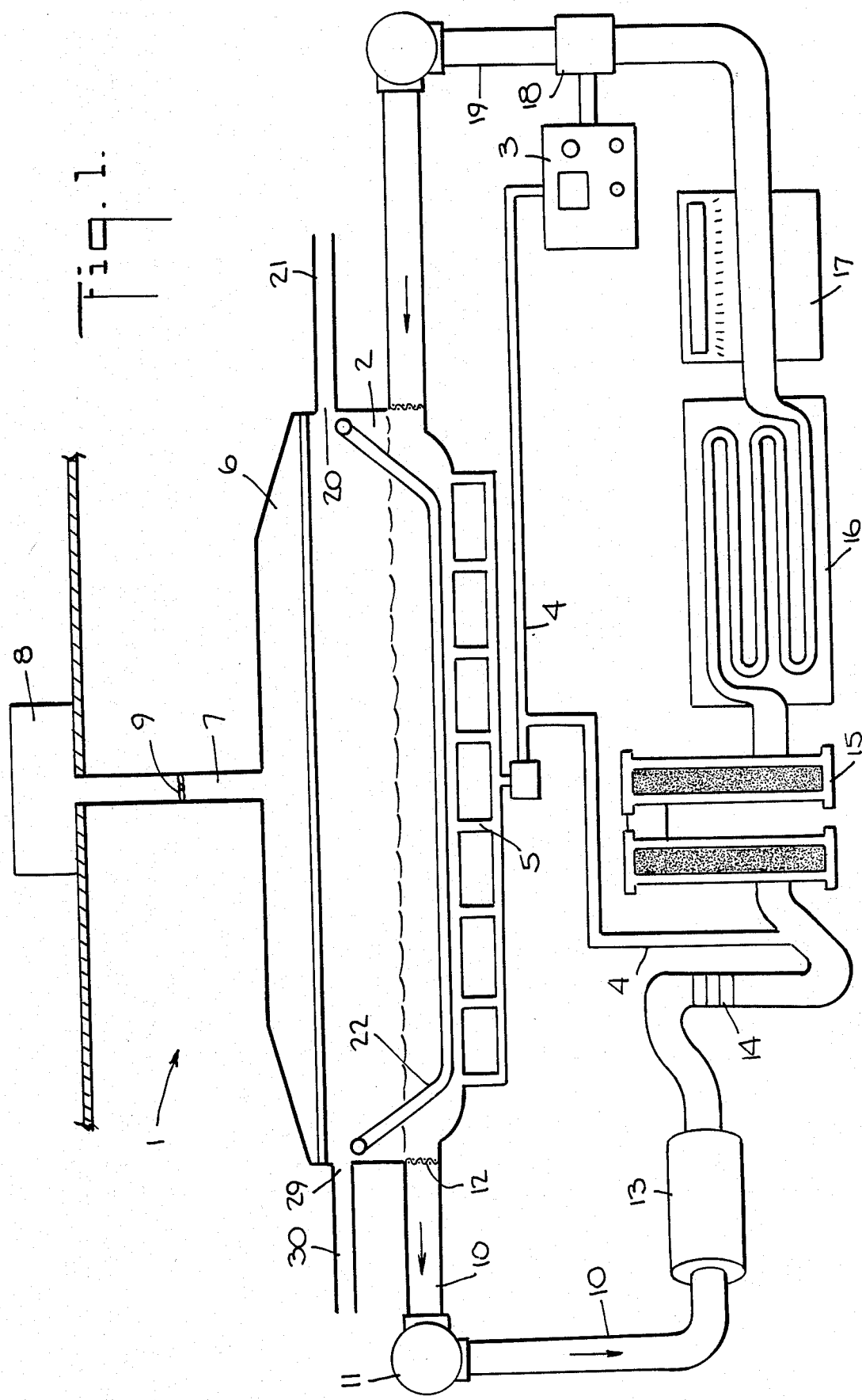
FIG. 1 is a planar view of a carcass chiller and sterilizer of the invention.

Referring to FIG. 1 a carcass chiller and sterilizer is generally depicted at 1. The chiller 1 includes a wash tank 2 for holding ozonated water, ice, and carcasses. The tank should be of a volume which is sufficient to hold enough water to treat all of the carcasses. In the case of poultry, the USDA provides that one-half gallon of water needs to be added for each bird placed in the chiller.

The wash tank 2 is preferably constructed of an inner shell of 12 gauge stainless steel which has been coated on the outside with 1.5 inches of urethane insulation followed by an outer shell of 16 gauge stainless steel.

An ozone generator 3 is provided as a source of ozone. The ozone generator should be one which has been approved by the USDA. The generator is preferably of a capacity which is sufficient to cause the concentration of ozone in the water to be at least 2 parts per million (ppm). A 2 lb./day generator is usually sufficient. The generator should be adjusted so that the desired ozone concentration level is maintained. Although it has been found that an ozone concentration in water of 0.2 to 10 ppm is generally sufficient to sterilize almost all microorganisms, a concentration of from about 2 ppm to 5 ppm is preferred.

The chiller 1 is provided with an ozone injection system 4 for injecting ozone into the water in the apparatus. The ozone injection system 4 carries ozone from ozone generator 3 to tank 2. Preferably, the ozone injection system 4 bubbles ozone into the water of tank 2 from a multiplicity of inlets 5 (not depicted) which are preferably evenly distributed along the underside of tank 2. The inlets 5 should be provided with one-way valves (not depicted) which allow gaseous ozone to enter the tank and which prevent water from leaving the tank via the inlets. The ozone injection system may also carry ozone to the outlet piping at various other points along the apparatus. Alternatively, the ozone injection system may be in the form of a static mixer which injects ozone gas into the water of the apparatus. The static mixer may be positioned along outlet piping 10 or inlet piping 19 of the apparatus as described hereinafter.

Tank 2 is provided with a cover or hood 6 to prevent ozone from escaping into the ambient area. Escape piping 7 emanates from an opening in the hood in order to allow excess ozone gas to escape from the tank. The escape piping leads to an ozone scrubber 8 which electronically destroys residual ozone before it is ejected into the atmosphere. The escape piping contains an exhaust fan 9 to draw ozonated air out of the tank and into the ozone scrubber.

Wash tank 2 is provided with outlet piping 10 on one end thereof. A pump 11 to draw water from the tank 2 into the outlet piping 10 is provided. Other pumps 11 may be distributed along the piping of the system to facilitate the flow of water therethrough. A screen 12, which permits the free flow of water therethrough, is positioned to block the exit end of tank 2 into outlet piping 10 to prevent carcasses from entering piping 10. Outlet piping 10 leads into a rotary screen filter 13 which is designed to filter scum, fat and other bulky carcass debris from the water in the outlet piping 10. The rotary screen filter 13 may be constructed of a wire mesh. The filter 13 should be cleaned from time to time to prevent the system from becoming clogged. To further inhibit clogging, screen filter 13 may be rotated. Also, the outlet piping 10 used around the vicinity of screen filter 13 may be of an enlarged diameter as compared to the piping of the rest of the system in order to prevent exceptionally slow movement of water through filter 13.

The outlet piping 10 leads from rotary screen filter 13 to a gyro vibrator filter 14 which is capable of filtering out contaminants on the order of 20 microns in diameter. Outlet piping 10 continues from gyro vibrator 14 to a diatomaceous earth cartridge filter 15. The diatomaceous earth filter 15 should be capable of filtering out particles as small as 8 microns. The outlet piping 10 in the region of the diatomaceous earth filter and gyro vibrator may be of an enlarged diameter as compared to the piping of the rest of the system in order to expedite movement of water therethrough. A two stage diatomaceous earth filter may be used in lieu of a one stage filter if it is so desired.

Outlet piping 10 continues from the diatomaceous earth filter 15 to a heat exchanger 16. Heat exchanger 16 chills the water to a temperature of 35 degrees Fahrenheit or below. Heat exchanger 16 may operate by glycol refrigeration. Because the heat exchanger cools the water of the system by refrigeration there is no need to add ice to the wash tank to maintain low temperatures.

Outlet piping 10 may lead from heat exchanger 16 to an ultraviolet light tube 17 where the water is further purified. Water emanating from the heat exchanger 16, or ultraviolet light tube 17, may pass through a static mixer 18 which ozonates the water with ozone from the ozone generator before the water is returned to wash tank 2. Preferably, another static mixer (not depicted) is positioned along outlet piping 10 between gyro vibrator 14 and diatomaceous earth filter 15 to ozonate the water of the system at another location.

Inlet piping 19 leads from heat exchanger 16, or ultraviolet light tube 17 (if present), or static mixer 18 (if present) to the entrance end of wash tank 2 which is opposite the end of the wash tank connected to outlet pipping 10. Another pump is preferably positioned along the inlet piping 19 to promote the flow of water into the tank. The sterilized and chilled water which is returned to wash tank 2 by means of the inlet piping 19 is ready to sterilize and chill the carcasses in the tank.

Carcasses enter the tank 2 through an entrance opening 20 in tank 2 located at an entrance end of the tank. The opening 20 should be located above the water level in the tank. Carcasses can be moved into the opening 20 of tank 2 by a conveyor means 21 which terminates at opening 20 and dumps carcasses into tank 2 through opening 20.

In a continuous process, carcasses can be moved through tank 2 in any of the conventional ways. For example, a standard conveyor 22 may be used such as one manufactured by Barker International for its model Mark IV poultry chillers. Alternatively, referring to FIGS. 2 and 3 a standard screw 23 may be rotatably attached on the inside of tank 2. Screw 23 should be a cylindrical shank having continuous helical ribs 24 threaded thereon. Adjacent helical ribs 24 define grooves 25. Adjacent helical ribs 24 should be spaced far enough apart from each other so that a carcass can fit in the grooves 25 between adjacent ribs. A motor 26 is provided to power the rotation of screw 23. As screw 23 rotates, carcasses 27 are pushed toward the exit end of tank 2 by helical ribs 24. When the screw means 23 is used to move carcasses through the tank, tank 2 should be provided with a channel 28 on the inside surface thereof for guiding carcasses 27 across the length of the tank. The turning of screw 23 also agitates the chiller water which enhances the diffusion of ozonated water into the carcasses where the ozone sterilizes all forms of bacteria and microorganisms. Water agitation also promotes moisture retention of the carcasses and more uniform cooling.

Once a carcass has been pushed by screw 23 or conveyor 22 to the exit end of tank 2 it can be removed from the tank in any of the conventional ways. For example, the conveyor means 22 near the exit end of tank 2 may be inclined for carrying the chilled carcasses up to an exit opening 29 in tank 2. Exit opening 29 should be located above the water level of the tank. Conveyor means 22 may also be powered by motor 26. Carcasses may be dumped out of the exit opening 29 onto another conveyor 30 for transporting the chilled carcasses to a packaging area.

It should be appreciated that other means may be employed for moving carcasses through tank 2. For example, a rotary conveyor and a rotary unloader manufactured by Barker International for its model Mark IV and Mark V poultry chillers may be used.

It should also be appreciated that the static mixers 18, heat exchanger 16 and ultraviolet light tube 17 may be located in positions with respect to each other, other than that which is described above without departing from the invention. For example, heat exchanger 16 may be located along the inlet piping 19 between ultraviolet light tube 17 and tank 2.

As seen from the foregoing description, the elements of the chiller are arranged in a continuous circuit to provide a closed system which purifies and recirculates chiller water. There is therefore no need to add water to the system to dilute contaminants. There is no need to add ice to the system because the water in the tank is chilled by refrigeration. When the system is cleaned, the water of the system presents no waste disposal problem because it has been sterilized.

What is claimed is:

1. An apparatus for chilling and sterilizing animal carcasses in ozonated water comprising:
   a wash tank capable of holding a quantity of water;
   piping means connecting an exit end of the wash tank to an entrance end of the wash tank;

a means for filtering out carcass debris from water, disposed along the piping means;
a means for ozonating water in the apparatus;
a means for cooling water in the apparatus;
a means for circulating water from the exit end of the wash tank, through the piping means and into the entrance end of the wash tank; and
a means for transporting carcasses through the wash tank.

2. An apparatus according to claim 1 wherein the means for cooling is a heat exchanger which operates by glycol refrigeration.

3. An apparatus according to claim 1 wherein the means for cooling is disposed along the piping means, between the means for filtering and the entrance end of the wash tank.

4. An apparatus according to claim 1 further comprising a wash tank hood which encloses the wash tank.

5. An apparatus according to claim 4 further comprising a means for drawing gas from the wash tank.

6. An apparatus according to claim 5 further comprising a means for decomposing gaseous ozone drawn from the wash tank by said means for drawing.

7. An apparatus according to claim 6 wherein the means for decomposing gaseous ozone is an ozone scrubber which operates electrically.

8. An apparatus according to claim 1 wherein the means for filtering is a rotatable screen filter.

9. An apparatus according to claim 1 wherein the means for filtering is comprised of a screen filter, a gyro vibrator filter and a diatomaceous earth filter which is capable of filtering fine particles of carcass scum and fat from water.

10. An apparatus according to claim 9 further comprising an ultraviolet light tube disposed along the piping means.

11. An apparatus according to claim 1 wherein the means for circulating water is a plurality of water pumps.

12. An apparatus according to claim 1 further comprising a means for agitating water located in the wash tank.

13. An apparatus according to claim 1 wherein the means for ozonating water in the apparatus comprises an ozone generator and a plurality of inlet valves, disposed along the underside of the wash tank, which permit ozone from the ozone generator to be injected into water in the wash tank.

14. An apparatus for chilling and sterilizing animal carcasses with ozonated water whereby contaminated water is purified and recirculated through the apparatus, comprising, in a closed system:
a wash tank capable of holding a quantity of water;
piping emanating from an exit end of said wash tank and running to an entrance end of said wash tank;
water filtering means disposed in said piping;
means for ozonating water in the apparatus;
means for cooling water in the apparatus;
means for drawing water out of the wash tank from the exit end thereof, into said piping and through said piping into the wash tank at the entrance end thereof;
means for drawing gas from said wash tank;
means for decomposing ozone in gas drawn by said means for drawing; and
means for liberating gas acted upon by said means for decomposing to the outside of the apparatus.

15. An apparatus according to claim 14 wherein said water filtering means comprises a screen filter which is capable of filtering carcass debris from water in the apparatus.

16. An apparatus according to claim 15 wherein said screen filter is detachable.

17. An apparatus according to claim 14 wherein said water filtering means comprises a screen filter, a gyro vibrator filter and a diatomaceous earth filter.

18. An apparatus according to claim 17 further comprising an ultraviolet light tube disposed along said piping.

19. An apparatus according to claim 14 wherein said means for ozonating water comprises an ozone generator and means for injecting ozone form the generator into water contained in said wash tank.

20. A method for chilling and sterilizing animal carcasses with ozonated water comprising the steps of:
immersing animal carcasses in a tank of ozonated water;
chilling and maintaining said ozonated water at temperatures below about 40° F;
circulating water out of the tank;
filtering carcass debris from water circulated out of the tank; and
recirculating filtered water back into the tank.

21. A method according to claim 20 further comprising the step of ozonating water in the tank.

22. A method according to claim 20 further comprising the step of maintaining the concentration of ozone in water above about 2 ppm.

23. A method according to claim 21 further comprising the steps of decomposing gaseous ozone contained in the tank and liberating the decomposed ozone to the outside of the tank.

24. An apparatus for chilling animal carcasses in water whereby the water used to chill the carcasses is continuously purified and recirculated through the carcasses comprising:
a wash tank capable of holding a quantity of water;
piping means connecting an exit end of the wash tank to an entrance end of the wash tank;
a means for filtering out carcass debris from water in the piping means;
a means for cooling water in the apparatus;
a means for sterilizing water in the apparatus; and
a means for circulating water from the exit end of the wash tank, through the piping means, and into the entrance end of the wash tank.

25. An apparatus according to claim 24 in which the means for sterilizing water is an ultraviolet light tube.

* * * * *